United States Patent [19]
Singer et al.

[11] Patent Number: 5,641,675
[45] Date of Patent: Jun. 24, 1997

[54] CIS-ACTING SEQUENCES FOR INTRACELLULAR LOCALIZATION OF RNA

[75] Inventors: Robert H. Singer, Shrewsbury; Edward H. Kislauskis, Kingston, both of Mass.

[73] Assignee: University of Massachusetts Medical Center, Worcester, Mass.

[21] Appl. No.: 319,836

[22] Filed: Oct. 7, 1994

[51] Int. Cl.$^6$ .............................. C12N 5/00; G07H 21/04
[52] U.S. Cl. .......................... 435/325; 435/375; 514/44; 536/23.1; 536/24.5; 935/33
[58] Field of Search ........................ 514/44; 435/172.1, 435/172.3, 240.1, 240.2; 536/23.1, 24.1, 24.5; 935/34, 33

[56] References Cited

FOREIGN PATENT DOCUMENTS

PCT/US95/13142  2/1996  WIPO.

OTHER PUBLICATIONS

R Weiss (1991) Science News 139: 108–109.
CA Stein et al (1993) Science 261:1004–1012.
JF Milligan et al. (1993) J Med Chem 36:1923–1937.
P Westermann et al (1989) Biomed Biochim Acta 48: 85–93.
N Miller et al (1994) Parasitology Today 10:92–97.
RA Stull et al (1995) Pharmaceutical Research 12: 465–483.
S Wu–Pong (1994) Pharmaceutical Technology 118: 102–114.
RW Wagner (1994) Nature 372:333–335.
TA Kost et al. (1983) Nucleic Acids Research 11: 8287–8301.
Kislauskis et al., "Sequences Required for Intracellular Localization of β–Actin Messenger RNA," *Mol. Biol. Cell*, 4:6a (supplement), abstract 29 (Oct. 1993).
Jackson, "Cytoplasmic Regulation of mRNA Function: The Importance of the 3' Untranslated Region", *Cell* 74:9–14 (1993).
Kim–Ha et al., "Multiple RNA Regulatory Elements Mediate Distinct Steps in Localization of *oskar* mRNA", *Development* 119:169–178 (1993).
Kislaukis et al., "Isoform–specific 3'–untranslated Sequences Sort α–cardiac and β–cytoplasmic Actin Messenger RNAs to Different Cytoplasmic Compartments", *J. Cell Biol.* 123:165–172 (1993).
Macdonald et al., "RNA Regulatory Element BLE1 Directs the Early Steps of *bicoid* mRNA Localization", *Development* 118:1233–1243 (1993).
Macdonald, "The Means to the Ends: Localization of Material Messenger RNAs", *Sem. Dev. Biol.* 3:413–424 (1992).
Singer, "RNA Zipcodes for Cytoplasmic Addresses", *Current Biol.*, 3:719–721 (1993).
Sundell et al., "Actin mRNA Localizes in the Absence of Protein Synthesis", *J. Cell Biol.* 111:2397–2403 (1990).
Wilhelm et al., "RNA on the Move: The nRNA Localization Pathway", *J. Cell Biol.* 123:269–274 (1993).
Kislaukis et al., "Sequences responsible for intracellular localization of β–actin messenger RNA also affect cell phenotype," *J. Cell. Biol.* 172:441–451 (1994).
Kost et al., "The nucleotide sequence of the chick cytoplasmis β–actin gene," *Nucleic Acids Research* 11:8287–8301 (1983).

*Primary Examiner*—Bruce R. Campell
*Attorney, Agent, or Firm*—Fish & Richardson P.C.

[57] ABSTRACT

Disclosed are the particular 3' noncoding nucleotide sequences (zipcode and zipcode elements) that cause β-actin mRNA (and β-actin protein synthesis) to be localized in specific regions of the cytoplasm. Also disclosed is the discovery that zipcode function can be fully inhibited by antisense oligonucleotides.

6 Claims, 9 Drawing Sheets

| CONSTRUCT | INSERT | PERIPHERAL LAC Z ACTIVITY | PERCENT (ST. DEV.) |
|---|---|---|---|
| | no insert | — | 5.6 (+/-2.2) |
| A | | ++ | 32.6 (+/-5.9) |
| B | | ++ | 29.4 (+/-4.0) |
| C | | ++ | 36.1 (+/-2.9) |
| D | | ++ | 36.1 (+/-4.1) |
| E | | — | 7.5 (+/-1.2) |
| F | | ++ | 33.0 (+/-6.1) |
| G | | ++ | 31.7 (+/-5.6) |
| H | | — | 9.5 (+/-3.2) |
| I | | — | 9.5 (+/-1.5) |
| J | | + | 14.1 (+/-2.6) |
| K | | +/- | 10.6 (+/-1.8) |
| L | | + | 16.6 (+/-1.7) |
| M | | — | 4.8 (+/-2.0) |
| N | (oppos. orient) | +/- | 11.3 (+/-6.7) |
| O | (31 nt deletion) | + | 20.9 (+/-6.0) |
| P | (2 nt deletion) | + | 17.9 (+/-6.9) |
| Q | (human) | ++ | 28.0 (+/-6.8) |

FIG. 2

|   | | Peripheral Localization Activity |
|---|---|---|
| (G) | taaACCGGACTGTTACCAACACCCCACCCCCTGTGATGAAACAAAAACCCATAAAATGC | ++ |
| (O) | taaACCGGACTGT--------------------------AACCCATAAATGC | + |
| (P) | taaACCGGACTGTTACCAACACCCCACCCCCTGTGATGAAACAAAAACCC--AAATGC | + |
| (L) | AAGTTCTACAATGCATCTGAGGACTTTGATTGTACATTTGTTT | + |

FIG. 3

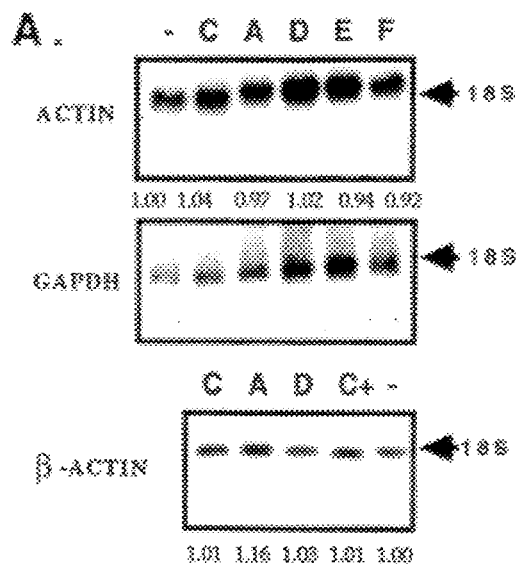
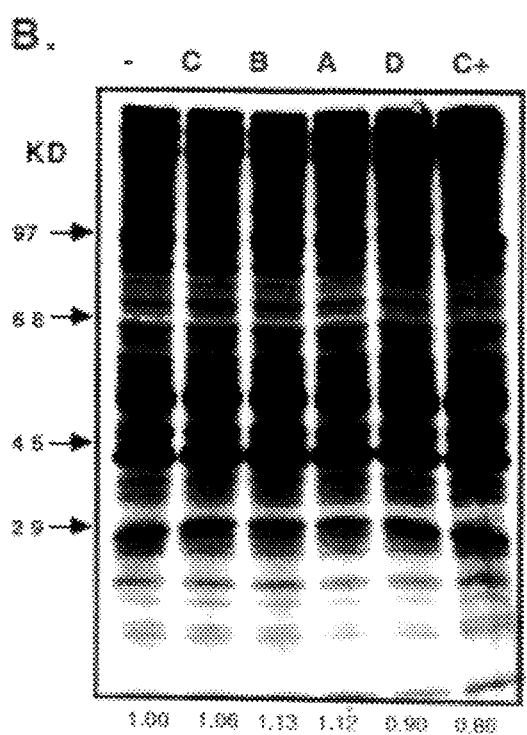
FIG. 6A
FIG. 6B

```
(ch)  ACCGGACTGTTACCAACACCC----ACACCCCTGTGATGAAACAAAAACCCATAAA--TGC
      ||||||  ||  |  |||||    ||||||  |   |||  |||||||  |||    |||
(hu)  G-CGGACTATGACTTAGTTGCCGTTACACCC--TTTCTTGA--CAAAACC--TAACTTGC
```

FIG. 8

CIS-ACTING SEQUENCES FOR INTRACELLULAR LOCALIZATION OF RNA

STATEMENT AS TO FEDERALLY SPONSORED RESEARCH

Work described herein was supported by National Institutes of Health grants AR41480 and HD18066.

FIELD OF THE INVENTION

This invention relates to the intracellular localization of nucleic acids and means for altering the intracellular localizaton of nucleic acids.

BACKGROUND OF THE INVENTION

Various mRNAs have been shown to localize in specific cytoplasmic regions (Singer, *Curr. Biol.* 3:919–721 (1993); Wilhelm et al., *J. Cell Biol.* 123:269–274 (1993)). Known examples of such mRNA localization fall into two major classes: cellular mRNAs transcribed in somatic (or zygotic cells); and maternal mRNAs that are asymmetrically positioned in oocytes, where they are involved in establishing embryonic axes.

Maternal mRNA localization is exemplified by oskar and bicoid mRNAs, which localize, respectively, at the posterior and anterior ends of Drosophila eggs (Macdonald, *Sem. Dev. Biol.* 3:413–424 (1992)). In Drosophila, mutations affecting the localization of the oskar and bicoid mRNAs are lethal.

Actin provides a useful model of mRNA localization in somatic cells. Actin is a highly abundant structural constituent of all eukaryotic cells. It is integral to a variety of cellular functions. In differentiating mammalian myoblasts, β-actin mRNA localizes to the leading lamellae, while α-actin localizes to a perinuclear compartment of the same cytoplasm (Kislauskis et al., *J. Cell Biol.* 123:165–172 (1993)).

As a major constituent of the cytoskeleton or myofilaments, actin is essential for the maintenance of cell polarity and motility (Bretcher, *Ann. Rev. Cell Res.* 7:337–374 (1991); Cooper, *Ann. Rev. Physiol.* 53:585–605 (1991); Levitt et al., *Mol. Cell Biol.* 7:2457–2466 (1987); Pollard et al., *Curr. Opin. Cell Biol.* 5:1–2 (1993)), intracellular transport (Kuznetsov et al., *Nature* 356:722–725 (1992)), protein synthesis (Hesketh et al., *Biochem. J.* 277:1–10 (19910; Negrutskii et al., *Proc. Natl. Acad. Sci. USA* 88:4991–4995 (1991); Yang et al., *Nature* 347:494–496 (1990)), enzymatic processes (Farwell et al., *J. Biol. Chem.* 265:18546–18553 (1990); Hunt et al., *Biochim. Biophys. Acta* 1043:19–26 (1990); Knull et al., *Curr. Top. Cell Regul.* 33:15–30 (1992); Sarndahl et al., *J. Cell Biol.* 109:2791–2799 (1989)), and mRNA localization (Singer, *Curr. Opin. Cell Biol.* 4:15–19 (1992); Sundell et al., *J. Cell Biol.* 111:2397–2403 (1991); Yisraeli et al., *Development* 108:289–298 (1990)) .

In chicken embryonic fibroblasts ("CEFs") and myoblasts, actin mRNA is highly localized at the leading lamellae, quite different from the distribution of mRNAs coding for either vimentin or tubulin (Lawrence et al., *Cell* 45:407–415 (1986)). In leading lamellae, rapid changes in actin polymerization drive extension of the lamellipodia (Carlier, *J. Biol. Chem.* 266:1–4 (1991); Cooper, supra; Wang, *J. Cell Biol.* 105:2811–2816 (1987)). Both β-actin protein and mRNA colocalize at the leading edge of endothelial cells in response to wounding (Hoock et al., *J. Cell Biol.* 112:653–664 (1991)) and in C2 myoblasts (Hill et al., *J. Cell Biol.* 122:825–832 (1993)). Thus, actin mRNA localization may facilitate the compartmentalization of actin synthesis (Singer, supra).

Cytoplasmic localization of maternal mRNAs depends on their 3' untranslated regions ("3' UTRs") (Jackson, *Cell* 74:9–14 (1993)). For example, a 50 nucleotide sequence, designated BLE1, found in the 680 nucleotide bicoid 3' UTR, has been implicated in bicoid mRNA localization (Macdonald et al., *Development* 118:1233–1243 (1993)).

Although the 3' UTRs of α-actin and β-actin mRNAs have been shown to be necessary and sufficient for proper cytoplasmic localization (Kislauskis et al., supra), those 3' UTRs are large, i.e., β-actin, 591 nucleotides; α-actin, 175 nucleotides. Which part (or parts) of the 3' UTR is responsible for the localization of β-actin mRNA (or any other cellular mRNA) to specific cytoplasmic regions has remained unknown.

SUMMARY OF THE INVENTION

We have discovered the particular 3' noncoding nucleotide sequences (zipcode and zipcode elements) that cause β-actin mRNA (and β-actin protein synthesis) to be localized in specific regions of the cytoplasm. We have further discovered that zipcode function can be fully inhibited by antisense oligonucleotides. Our discoveries enable the specific alteration of an existing cellular phenotype, by inhibiting the function of endogenous zipcodes. Advantageously, this alteration of phenotype is accomplished without suppressing the expression of any endogenous genes or expressing any exogenous genes. Our discoveries also provide for the gene products of exogenous genes to be advantageously translated in particular cytoplasmic regions.

Accordingly, in one aspect, the invention features a method for inhibiting the intracellular localization of a target mRNA molecule, comprising introducing into a target cell an antisense oligonucleotide. In another aspect, the invention features a method for directing the intracellular localization of an mRNA molecule, comprising incorporating into the mRNA a cis-acting nucleotide sequence, i.e., a zipcode or zipcode elements. In related aspects, the invention features isolated DNA molecules consisting of naturally-occurring zipcodes; artificial zipcodes, which comprise, within a span of about 50 contiguous nucleotides, two or more zipcode elements; and zipcode antisense oligonucleotides.

As used herein, "zipcode" means a nucleotide sequence whose presence in the 3' UTR of an mRNA molecule results in the localization of the mRNA molecule to a specific region (or regions) of the cytoplasm of a eukaryotic cell.

As used herein, "artifical zipcode" means a nucleotide sequence that: (1) comprises two or more zipcode elements as defined herein; (2) is not known to occur in naturally-occurring mRNAs; and (3) functions to localize mRNA transcripts into which it is incorporated. In an artificial zipcode, the zipcode elements need not be in any particular order, nor have any particular spacing arrangement with respect to each other to contextual sequences.

As used herein, "zipcode element" means a minimal zipcode nucleotide sequence motif displaying mRNA localization activity.

As used herein, "mRNA localization" means a nonuniform distribution of mRNA molecules within a cell's cytoplasm, such that the nonuniformity is discernible by in situ hybridization methods known in the art. Once colocalization of mRNA transcribed from a reporter gene and activity of the reporter gene product has been confirmed by in situ hybridization, localization of the mRNA may be inferred thereafter by observing localization of the activity of the reporter gene product.

As used herein, "reporter gene" means a gene whose expression may be assayed; the term reporter gene includes, but is not limited to, β-glucuronidase (GUS), luciferase, chloramphenicol acetyltransferase (CAT), β-galactosidase (Lac Z), and green fluorescent protein (GFP) (Chalfie et al., Science 263:802–805 (1994).

As used herein, "target cell" means a eukaryotic cell containing transcripts whose localization is to be inhibited. A target cell may be in vivo, i.e., comprised within an organ or tissue of a living animal or human. A target cell may also be in vitro, i.e., a cultured animal cell, cultured human cell, or cultured eukaryotic microorganism.

As used herein, "target mRNA" means an mRNA whose localization is to be inhibited.

As used herein, "target zipcode" means a zipcode whose localization activity is to be inhibited by an antisense oligonucleotide having a sequence complementary to part or all of the zipcode.

DETAILED DESCRIPTION

In order that the invention herein described may be more fully understood, the following detailed description is set forth. The drawings will first be described.

Drawings FIG. 1A is a schematic depiction of the expression plasmid, RSVβgal, used in the zipcode bioassay.

FIG. 2 is a schematic representation of DNA constructs used to map cis-acting localization sequences in the chicken β-actin 3' UTR. Designated schematically are vector RSVβgal polylinker sequences (solid filled box); β-actin coding sequences (diagonally hatched box); and β-actin 3' UTR (solid line). The position of the 54 nucleotide zipcode and the 43 nucleotide zipcode element-containing region within the 3' UTR are indicated with vertical dotted lines.

FIG. 3 is a depiction comparing: the nucleotide sequence of the chicken β-actin zipcode (localization activity ++) consisting of the first 54 nucleotides of the 3' UTR, i.e., positions 1222–1278 (G); a zipcode construct with a 31-nucleotide internal deletion which reduced its activity from ++ to + (O); a zipcode construct with a 2-nucleotide internal deletion which reduced its activity from ++ to + (P); and the 43-nucleotide chicken β-actin sequence containing zipcode elements (localization activity +), i.e., positions 1412–1452. Shared sequence motifs are indicated by wedges. The letter designations of the sequences correspond to the designations of the constructs in FIG. 2.

Figure 4:
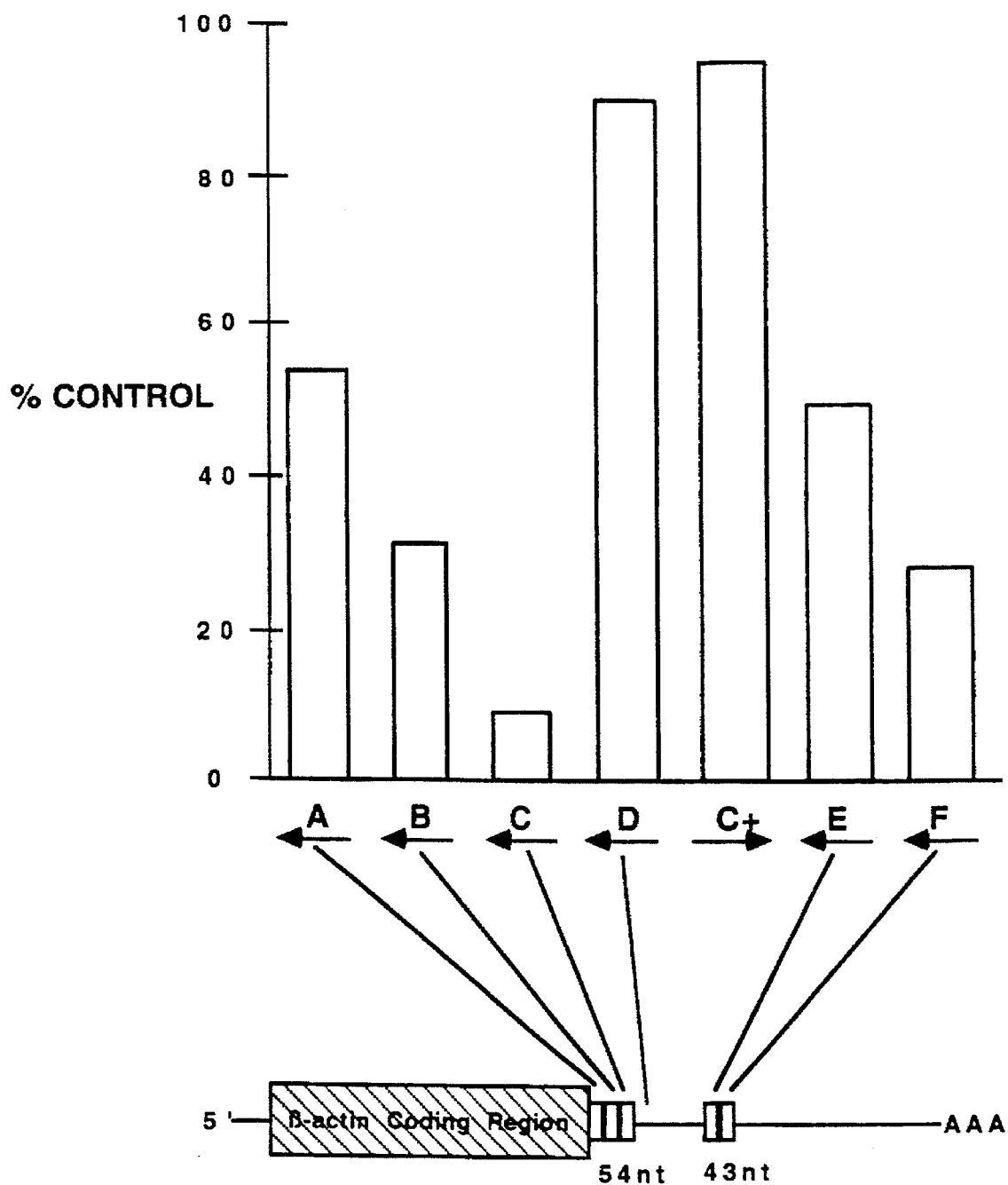

FIG. 4 is a bar graph summarizing the effect of antisense oligonucleotide treatment on endogenous β-actin mRNA localization in cultured CEFs, relative to localization in a non-treated CEF control culture. Oligonucleotides A–F are antisense oligonucleotides based on the regions of the β-actin 3'UTR indicated by the mRNA map beneath the bar graph. Oligonucleotide C+ is a sense oligonucleotide corresponding to antisense oligonucleotide C. The percent of CEFs with localized endogenous β-actin was determined by in situ hybridization after a 12-hour treatment with each oligonucleotide at a concentration of 8 μM.

Figures 5A, 5B:
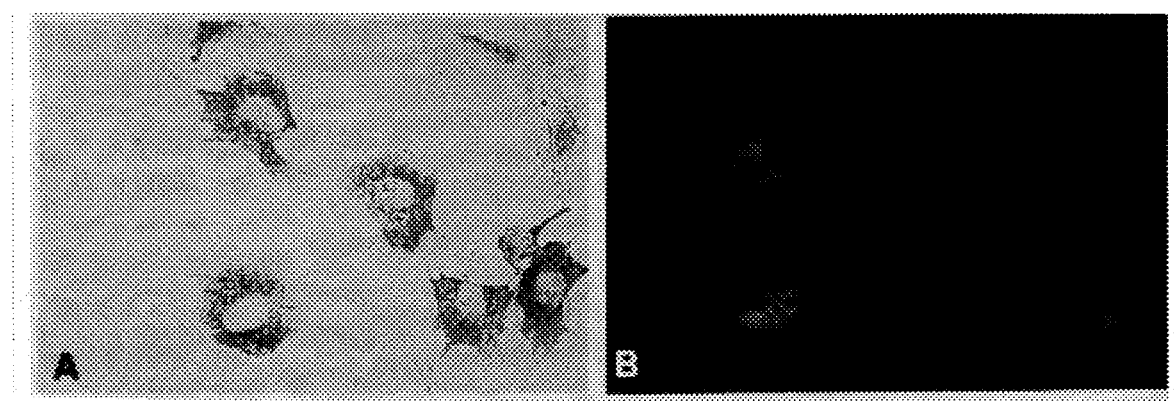

FIG. 5A is a photograph of CEFs treated for 12 hours with oligonucleotide C and subjected to in situ hybridization.

FIG. 5B is a photograph of CEFs treated for 12 hours with oligonucleotide C and subjected to staining with FITC-phalloidin and DAPI.

Figures 5C, 5D:
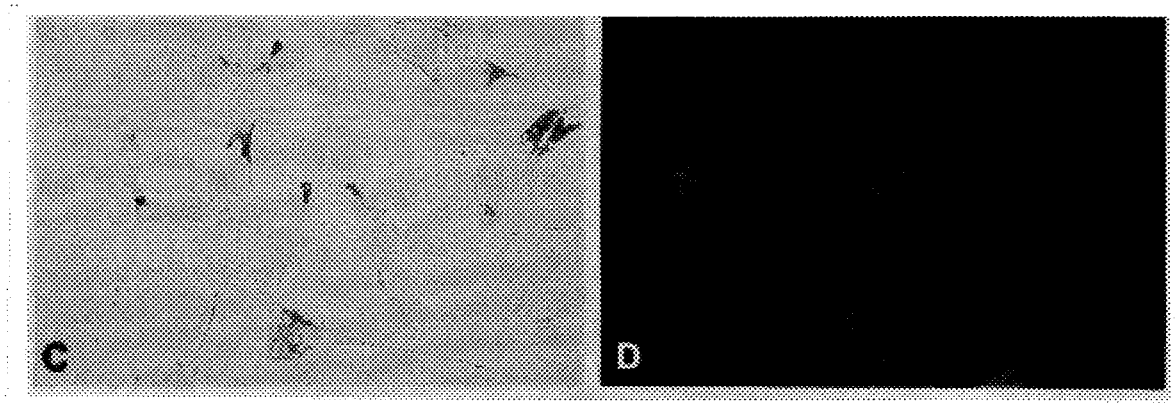

FIG. 5C is a photograph of CEFs treated for 12 hours with oligonucleotide C+ and subjected to in situ hybridization.

FIG. 5D is a photograph of CEFs treated for 12 hours with oligonucleotide C+ and subjected to staining with FITC-phalloidin and DAPI.

Figures 5E, 5F:
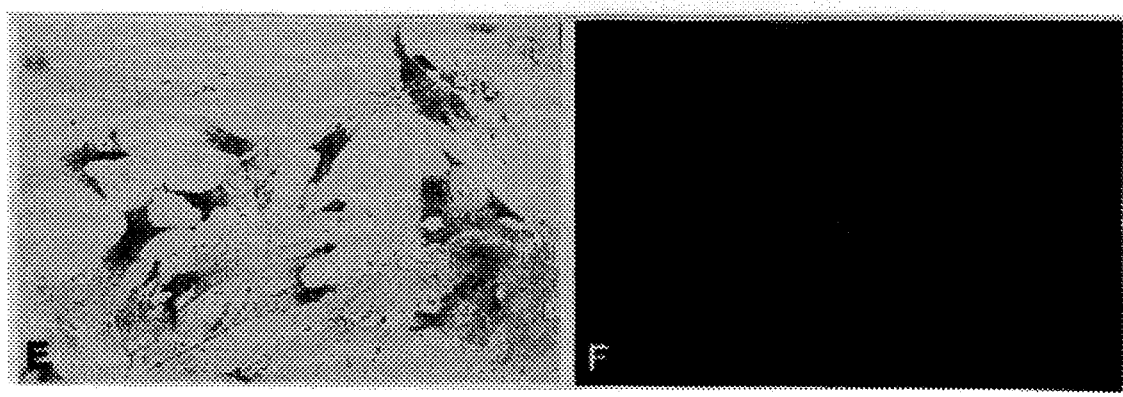

FIG. 5E is a photograph of CEFs treated for 12 hours with oligonucleotide D and subjected to in situ hybridization.

FIG. 5F is a photograph of CEFs treated for 12 hours with oligonucleotide D and subjected to staining with FITC-phalloidin and DAPI.

Figures 5G, 5H:
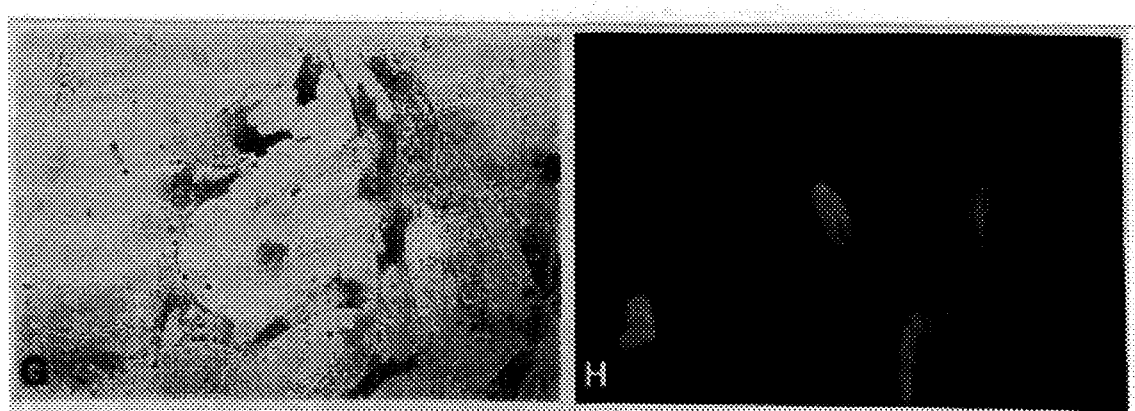

FIG. 5G is a photograph of control CEFs subjected to in situ hybridization, without antisense oligonucleotide treatment.

FIG. 5H is a photograph of control CEFs subjected to staining with FITC-phalloidin and DAPI, without antisense oligonucleotide treatment.

FIG. 6A is a depiction of Northern blots. The upper panel shows an analysis of total RNA from control cells (dash mark), or from cells treated for 12 hours (three treatments of 4 hours each) with oligonucleotides C, A, D, E or F (8 μM). The probe was a β-actin cDNA covering nucleotide positions 95–1477. The middle panel shows an internal standard consisting of total RNA from the same cells, probed with GAPDH cDNA. The lower panel shows total RNA probed with a β-actin 3' UTR-specific probe. The numbers below each lane represent the ratio of hybridized RNA in the treatment to hybridized RNA in the control.

FIG. 6B is a depiction of protein analyses. The upper panel shows an SDS-PAGE autoradiogram of total-labeled proteins extracted from control cells (–), and cells treated for 12 hours with oligonucleotides A–D and C+ (8 μM), after a 30 minute pulse with [$^{35}$S]methionine. The numbers below each lane represent the ratio of actin (43 kD) to the 29 kD band.

Figure 7:
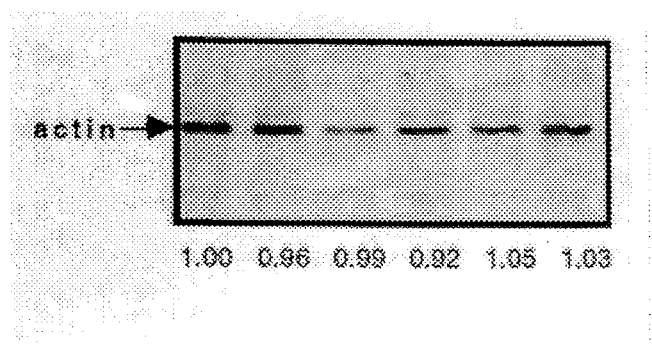

FIG. 7 is a depiction of an SDS-PAGE immunoblot analysis performed with a β-actin-specific antibody. The lanes contain proteins extracted from control cells (–), and cells treated for 12 hours with oligonucleotides A–D and C+ (8 μM), after a 30 minute pulse with [$^{35}$S]methionine. The numbers below each lane represent the ratio of immunoreactive material in the treatment to immunoreactive material in the control.

FIG. 8 is a comparison of the sequences of the first 54 nucleotides in the chicken (SEQ ID NO:1) and human (SEQ ID NO:31) β-actin gene 3'UTRs.

In a preferred embodiment of the present invention, a zipcode is a cis-acting sequence of 54 nucleotides consisting of (SEQ ID NO:1). In another preferred embodiment, a zipcode element-containing sequence is a cis-acting sequence of 43 nucleotides consisting of (SEQ ID NO:2). Either the 54 nucleotide zipcode, or the 43 nucleotide zipcode element-containing sequence, or both, may be incorporated into a recombinant DNA construct so as to be included in an mRNA molecule transcribed from the DNA construct.

As described in detail below, applicants have discovered that features possessed in common by the 54- and 43-nucleotide cis-acting mRNA localization sequences are motifs, i.e., short substituent sequences, hereinafter referred to as "zipcode elements." Applicants have further discovered that zipcode elements are able to direct mRNA localization when incorporated into nucleotide contexts other than those in which they naturally occur.

Accordingly, in another preferred embodiment of the present invention, an artificial zipcode consists of two or more zipcode elements comprised within a span of about 50 nucleotides. While we describe herein only a limited number of particular artifical zipcodes, it is apparent that our discovery of zipcode elements enables one of ordinary skill in the art to construct numerous other artifical zipcodes by varying parameters such as the total number, the order, the spacing and the nucleotide context of the zipcode elements. Such additional artificial zipcodes are within the scope of the present invention.

Preferably, the zipcodes of this invention are placed in a non-coding region of an mRNA. More preferably, the zipcodes are placed in the 3' untranslated region ("3' UTR"), 5' to the poly(A) tail of the mRNA. Within the 3' UTR, there is considerable latitude in the placement of the zipcode. For example, in one embodiment the 5' end of the 54 nucleotide zipcode is located directly adjacent to the stop codon at the 3' end of the lac Z gene. On the other hand, in another embodiment, the 5' end of the 43 nucleotide sequence containing zipcode elements is located 190 nucleotides downstream (3') from the stop codon.

We have discovered that hybridization of an antisense molecule with a zipcode in the 3' UTR of an mRNA inhibits the normal functioning of the zipcode. As a result, the zipcode-containing mRNA does not display its normal cytoplasmic localization. Accordingly, another preferred embodiment of the present invention is a method for inducing mislocalization or nonlocalization of an otherwise localized mRNA, through the use of antisense oligonucleotides. This ability to inhibit the normal localization of an mRNA advantageously allows the modulation of cell phenotype or behavior without suppressing the expression of any genes or requiring the expression of any new genes.

A preferred embodiment of the present invention is an antisense molecule that binds to the zipcode of an mRNA through complementary base pairing. The particular zipcode site to which the antisense molecule binds, and the length of the antisense molecule will vary according to factors including, but not limited to, the following: the number of zipcodes in the target mRNA, the length of the target zipcode(s), the nucleotide sequence of the target zipcode(s), the degree of localization inhibition desired, whether the antisense molecule is transcribed in vivo or added exogenously.

Preferably the antisense molecule is between 5 and 100 nucleotides in length. More preferably, the antisense molecule is between about 10 and 50 nucleotides in length. The antisense molecule may consist of a single nucleotide sequence. Alternatively, the antisense molecule may comprise a repetitive sequence, wherein two or more repetitive sequences are in tandem, so that a single antisense molecule may bind to a plurality of target mRNA molecules.

If the antisense molecule is an RNA transcribed in vivo, from an antisense DNA construct, the antisense DNA construct will comprise a coding sequence (encoding the antisense RNA molecule) operatively linked to regulatory sequences, including a promoter and a transcription termination signal. In some embodiments of this invention, the promoter controlling transcription of the antisense sequence may be constitutive. In other embodiments, it may be desirable to place transcription of the antisense sequence under the control of an inducible promoter. Then, the inhibition of localization of the target mRNA could be modulated by the presentation of an inducer of the promoter. For example, where it is desirable to inhibit mRNA localization only at a particular point in time, or in a specific cell type or tissue type of a transgenic animal, it may be advantageous to have the antisense construct present in all cells of the animal and target the inducer, to achieve the desired specificity in antisense expression.

Exogenous antisense oligonucleotides may, but need not necessarily, comprise modified nucleotides. The nucleotides may be modified before or after polymerization. The modification may be at a variety of locations along the length of the oligonucleotide. For example, the oligonucleotide may be modified at the 5' end, the 3' end, or both. In addition, the internal phosphate groups or the bases may be modified.

Modification of the nucleotides in the antisense oligonucleotide may be desirable for purposes such as facilitating antisense oligonucleotide entry into target cells, increasing stability of antisense-sense hybrids formed in the target cell, or increasing the antisense oligonucleotide's persistence in the target cell, by decreasing its susceptibility to nuclease degradation. In a preferred embodiment of the present invention, an antisense oligonucleotide comprises one or more phosphorothioate nucleotides. In phosphorothioate nucleotides, one of the non-bridging oxygen atoms in the phosphate portion of the nucleotide is replaced by a sulfur atom. The use of phosphorothioate nucleotides is known in the art (see, e.g., U.S. Pat. No. 5,264,423; or Eckstein, Ann. Rev. Biochem. 54:367–402 (1985)).

Exogenous antisense oligonucleotides may be introduced into target cells or tissues for research purposes or therapeutic purposes. The preferred method of introducing the antisense oligonucleotides into target cells or tissues will depend on considerations such as whether the cells or tissues are in vitro or in vivo. The preferred method of introducing the antisense oligonucleotides into target cells or tissues in vivo may depend on whether the target cells or tissues are in an animal or human.

Various methods for introducing nucleic acids, including antisense oligonucleotides, into cultured eukaryotic cells are known in the art. Examples of such methods are calcium phosphate transfection, liposome mediated transfection, and electroporation. Reagents and kits for introducing nucleic acids into cultured cells are commercially available. In a preferred embodiment of the present invention, "Lipofectin Reagent" (GIBCO-BRL, Gaithersburg, Md.) is used to introduce nucleic acid molecules into eukaryotic cells in vitro.

Methods for introducing nucleic acid molecules, including antisense oligonucleotides, into cells and tissues in vivo, for research purposes and for therapeutic purposes are known in the art. See, for example, Bayever et al., "Oligonucleotides in the Treatment of Leukemia", Hematol. Oncol. 12:9–14 (1994); and Schreier, "The New Frontier: Gene and Oligonucleotide Therapy", Pharm. Acta Helv. 68:145–159 (1994) .

The various DNA molecules used in the practice of the present invention, including zipcode constructs, constructs encoding antisense RNA molecules, directly synthesized antisense oligonucleotides, transformation vectors, and the like can be obtained by application of recombinant DNA techniques well known in the art. See generally, Sambrook et al., Molecular Cloning, 2d ed., Cold Spring Harbor Press (1989); and Ausubel et al., Current Protocols in Molecular Biology, Wiley Interscience (1989).

The present invention may be used therapeutically or diagnostically. For example, certain diseases, such as some forms of cancer, may result from a change in the normal distribution of a critical protein, such as actin. Major changes in actin abundance or actin-associated proteins can affect cell division or differentiation, or both (Rao et al., *Cancer Res.* 50:2215–2220 (1990); Pienta et al., *Cancer Res.* 49:2525–2532 (1989); Cunningham et al., *Science* 255:325–327 (1992)). A major characteristic that differentiates malignant tumors from benign ones is their invasiveness. The invasiveness of the cells of human metastatic melanomas, rat prostatic adenocarcinomas (e.g., Dunning R327) correlates with motility (Byers et al., *Am. J. Pathol.* 139:423–435 (1991); Raz, *Exp. Med. Biol.* 233:227–233 (1988)). In turn, motility depends on, among other factors, peripheral localization of β-actin biosynthesis. Thus, by providing a means to delocalize β-actin biosynthesis, the present invention provides an avenue by which to modulate or inhibit cell motility and associated metastasis.

Another example of a disease related to mislocation of mRNA is myotonic distrophy, a dominant inherited genetic disease with mostly neuromuscular effects. It belongs to a class of diseases caused by the expansion, within a gene, of a repeated nucleotide triplet sequence. Examples of other diseases resulting from the expansion of a trinucleotide repeat are Huntington's, Fragile X, and spinobulbar muscular distrophy. The expanded trinucleotide repeat associated with myotonic distrophy occurs in the 3' UTR of the MtPK gene on chromosome 19.

We have found that the MtPK gene transcripts containing the repeat expansion accumulate in the nuclei of fibroblasts and muscle cells of myotonic distrophy patients, but not in the corresponding cells of normal individuals. Thus, the expanded trinucleotide repeat disrupts the normal movement of MtPK mRNA from the nucleus into the cytoplasm. Accordingly, myotonic distrophy, and other diseases of its class, are candidates for zipcode-related gene therapy.

The present invention may be used industrially. For example, a zipcode may be incorporated into a genetic construct for the production of a recombinant protein in a transformed eukaryotic host cell. The resulting localization of the recombinant protein production within a particular host cell cytoplasmic region could have advantages such as reduced toxicity to the host cell, enhanced secretion of the recombinant protein, or facilitation of the collection and purification of the recombinant protein.

In addition, the present invention may be advantageously used as a tool for modulating intracellular mRNA localization in medical and biological research. For example, the present invention enables the experimental simulation of mRNA mislocalization-related diseases such as myotonic distrophy, in cells grown in vitro.

Bioassay for Determination of Zipcode Activity

We developed a bioassay to detect and quantify the ability of a given nucleotide sequence to direct cytoplasmic localization of an mRNA encoding a heterologous reporter molecule. We used the bioassay to identify and compare zipcodes in the 3' UTR of β-actin mRNA. We also used the bioassay to evaluate artificial zipcodes. The bioassay, described in detail in Kislauskis et al. (supra), is briefly described below.

At the heart of the assay is an expression vector, RSVβgal, which is used to produce a fusion transcript, but not a fusion protein. The fusion transcript encodes the reporter gene product, β-galactosidase. The β-actin 3'UTR sequences to be evaluated were inserted into the polylinker between the Lac Z termination codon and SV-40 3'UTR, in the RSVβgal vector. Following a period of transient expression, β-galactosidase-positive transfectants were detected in fixed cells using the chromogenic substrate X-gal.

Since β-galactosidase is functional as a homodimer or tetramer of 135-kD subunits, it diffuses slowly in the cytoplasm and serves as a reasonable indicator of the distribution of its cognate mRNA. Transfectants were scored as "peripheral", "perinuclear" or "non-localized", according to where the majority of the β-galactosidase activity (blue stain) appeared in the cytoplasm. Non-localized cells showed a uniform distribution of blue stain; perinuclear cells had most of their stain associated with the nucleus; and peripheral cells had blue stain separated from the nucleus and in the leading lamellae.

In situ hybridiation was performed using LacZ specific probes to verify that the distribution of LacZ mRNA correlated with the distribution of blue stain in transfectants. The in situ hybridization product (black) in a cell transfected with a reporter construct containing the entire β-actin cDNA sequence colocalized with the blue staining in the lamellae. In negative controls, consisting of the assay vector comprising the β-galactosidase reporter gene without an actin 3' UTR sequence, the β-galactosidase activity was not localized in a statistically significant number of cells relative to zipcode-containing constructs. In controls wherein the Lac Z gene was fused to the 5' UTR plus the coding region of either β-actin or α-actin, the transfected cells showed no significant difference from the negative control involving the vector alone. Cells transfected with a construct containing the α-cardiac actin 3' UTR showed a significant increase in perinuclear β-galactosidase activity.

The percent of cells which showed peripheral localization of the enzymatic activity was quantitatively monitored and provided a rigorous evaluation of each construct. Each construct (A–N) was evaluated in 3–20 independent experiments with 300 to several thousand transfected (blue) cells counted per experiment. Transfectants were scored as localized or non-localized based on whether the cytoplasmic distribution of blue staining was peripheral or non-localized. The percent of transfectants with peripheral blue staining was calculated for each experiment. The activity was summarized for each construct based on statistical significance: (++) greater than 28%; (+) 14–28%; (+/–) 1–14%; and (–) less than 10%.

Plasmid Constructions

As used herein, "RSVβgal" refers to a derivative of the original RSVβgal plasmid. We produced our RSVβgal derivative by a single modification. That modification was the removal of a 250 base DraI/BamHI fragment containing a consensus polyadenylation signal upstream of the polylinker used in the constructions. The Rous Sarcoma Virus long terminal repeat (RSV LTR) drives the expression of the reporter gene. The reporter gene encodes β-galactosidase from the bacterial Lac Z operon fused to SV-40 processing signals. In this vector, the SV-40 sequences contain two consensus polyadenylaton signals downstream of the RSVβgal polylinker. Plasmid constructions were verified by restriction endonuclease analysis and dideoxy sequencing.

The original RSVβgal plasmid is well-known and widely used in the art. Although we used the original RSVβgal as a starting material, it should be appreciated that other plasmids may be substituted as starting material for the DNA constructs described below. One acceptable substitute is commercially available as "pSVβ" (Clontech, Palo Alto, Calif., catalog no. 6178-1). The pSVβ vector is essentially the same as RSVβgal, except that it contains a different promoter, i.e., SV40 promoter instead of rous sarcoma virus promoter. The pSVβ vector can be modified by the removal of the 250 base DraI/BamHI fragment, as described above.

The steps for obtaining the particular constructs depicted in FIG. 2 are set forth below.

Construct A: The first step was ligating BamH I linkers (GIBCO BRL, Gaithersburg, Md.) to the complete 1814 bp Pst I fragment containing the full-length cDNA clone for chicken cytoplasmic β-actin (Cleveland et al., *Cell* 20:95–105 (1980)). The linker-bearing fragment was then ligated inserted into the BamH I site of the RSVβgal polylinker.

Construct B: The first step was to use exoIII/mungbean nuclease (Promega, Madison, Wis.) on the 1814 bp Pst I fragment containing the full-length β-actin clone, for 3'→5" deletion of nucleotides to position 1452. The exonuclease digestion product was a 233 nucleotide fragment of the 3' UTR. Then BamH I linkers were added to the 233 nucleotide digestion product. The resulting linker-bearing fragment was inserted into the BamH I site of the RSVβgal polylinker.

Construct C: A fragment containing β-actin nucleotides 1–1278 was obtained by cleaving the 1814 bp Pst I fragment (containing the full-length β-actin clone) with restriction endonuclease Fsp I. An Xba I linker was added at the Fsp I end of the fragment, and a BamH I linker was added at the opposite end. The linker-bearing fragment was then inserted, as a BamH I-Xba I fragment, into the RSVβgal polylinker.

Construct D: A fragment containing β-actin nucleotides 1193–1814 was obtained by cleaving the 1814 bp Pst I fragment (containing the full-length β-actin clone) with restriction endonuclease Ava II. BamH I linkers were added, and the linker-bearing fragment was inserted into the BamH I site of the RSVβgal polylinker.

Construct E: A fragment containing β-actin nucleotides 1–1192 was obtained by cleaving the 1814 bp Pst I fragment (containing the full-length β-actin clone) with restriction endonuclease Ava II. BamH I linkers were added, and the linker-bearing fragment was inserted into the BamH I site of the RSVβgal polylinker.

Construct F: The 1814 bp Pst I fragment (containing the full-length β-actin clone) was digested with restriction endonuclease Mbo I to release a 483 nucleotide Mbo I fragment, which was ligated into the BamH I site of RSVβgal.

Construct J: The BamH I-Xba I fragment of construct E was joined to an Xba I-Not I fragment generated by PCR, using the upper primer (SEQ ID NO:3) and the lower primer, (SEQ ID NO:4). The fragment so generated corresponds to β-actin nucleotides 1275–1778.

Construct K: This was constructed from a PCR-generated fragment using the upper primer (SEQ ID NO:5) and the lower primer (SEQ ID NO:6), which converted the Fsp I site at position 1278 to an Xba I site and generated a 507-bp Xba I-Not I fragment.

Construct M: This construct, the double mutant, was synthesized by connecting construct E with two PCR-generated fragments: one corresponding to positions 1278–1419 as a 153-bp Xba I-Hind III fragment using the upper primer (SEQ ID NO:7) and the lower primer (SEQ ID NO:8); and the other, corresponding to positions 1453–1778 as a 337-bp Hind III-Not I fragment, using the upper primer (SEQ ID NO:9) and the same lower primer used to create construct K.

Constructs G–I, L and N–Q: The necessary complementary pairs of oligonucleotides with flanking restriction sites (BamH I at 5' end, and Xba I at 3' end) were obtained by automated chemical synthesis of the individual strands. This allowed for directional cloning into the vector, once the complementary pairs were annealed. The pairs of annealed oligonucleotides for the constructs were as follows: Construct G, (SEQ ID NO:10) and (SEQ ID NO:11); Construct H, (SEQ ID NO:12) and (SEQ ID NO:13); Construct I, (SEQ ID NO:14) and (SEQ ID NO:15); Construct L, (SEQ ID NO:16) and (SEQ ID NO:17); and Construct Q, (SEQ ID NO:18) and (SEQ ID NO:19).

Zipcode elements, i.e., oligonucleotide motifs, were chemically synthesized, annealed and ligated into the polylinker, as above. The GGACT motif was comprised within the following two complementary strands:

5' GATCCTAAAC CGGACTGTA 3' (SEQ ID NO:20); and

5' AGTCTACAGT CCGGTTTAG 3' (SEQ ID NO:21).

The AATGC motif was comprised within the following two complementary strands:

5' GATCCAACCC ATAAATGCA 3" (SEQ ID NO:22); and

5' GATCTGCATT TATGGGTTG 3' (SEQ ID NO:23).

Cell Culture

Twelve day-old chicken embryonic fibroblasts (CEFs) prepared using standard techniques, were cultured onto gelatin-coated coverslips as described by Lawrence et al. (*Dev. Biol.* 133:235–246 (1989)) and Sundell et al. (*Cell Biol.* 111:2397–2403 (1990)). Cells on coverslips were washed with HBSS, fixed for 15 minutes at room temperature in 4% paraformaldehyde in PBS/5 mM MgCl$_2$, washed again in PBS, and, when necessary, stored in 70% ethanol at 4° C.

In Situ Hybridization

To detect endogenous actin mRNAs, coverslips were hydrated in PBS/5 mM MgCl$_2$, and then hybridized for two h at 37° C. with the mixture of oligonucleotide probes: α-specific (four probes, 5 ng/probe) and β-specific (six probes, 5 ng/probe) in 50% formamide containing 2×SSC, 0.2% BSA, 10% dextran sulfate, 2 mM vanadyl adenosine complex, and 1 mg/ml each of *Escherichia coli* tRNA and salmon sperm DNA. This mixture of oligonucleotide probes increases signal intensity (Taneja et al., *J. Cell Biochem.* 44:241–252 (1990)). After hybridization and washing successively for 30 min in 50% formamide/2×SSC at 37° C., 30 min in 50% formamide/1×SSC at 37° C., and 30 min in 1×SSC, coverslips were mounted on the slides using phenylene diamine (antibleaching agent) in 90% glycerol and PBS. To detect Lac Z reporter mRNAs, each coverslip was hybridized for 3 h at 37° C. to 20 ng of digoxigenin-labeled, nick-translated probes generated from the entire RSVβgal plasmid. For methods where that enzyme activity and the reporter mRNA were detected simultaneously, nick-translated probes were generated using standard procedures (Lawrence and Singer, 1989). After in situ hybridization, coverslips were washed three times in 1×SSC for 15-min each, then incubated with an anti-digoxigenin mouse IgG$_1$ mAB (Boehringer Mannheim Biochemicals, Indianapolis, Ind.) at a 1:25 dilution in 1×SSC for 1 h at 37° C. For detection, a second incubation with a 1:8 dilution of the AuroProbe™ One GAM 1 nM gold-labeled goat anti-mouse IgG (H+L) (Amersham Intl., Buckinghamshire, U.K.), followed by several washes with 1×SSC, a final wash with water, and 18 min of development with equal volumes of IntenSE™ M Silver Enhancement Reagents A and B (Amersham Intl.).

Transfection

CEFs were plated onto gelatin coated coverslips (22×22 mm) essentially as described above, with the following exceptions: cells were plated at a density of 1×10$^6$ cells/100 mm plate in OPTI-MEM (BRL-GIBCO, Gaithersburg, Md.) supplemented with 10% FBS and 2% chicken embryo extract. At about 50% confluence (24–48 hours), the cells were washed with HBSS and incubated for 12 hours in 10 ml of OPTI-MEM containing 20 µg of cesium-purified plasmid DNA with 30 µg Lipofectin (BRL-GIBCO) at 37° C. Subsequently, the medium was replaced with 10 ml of OPTI-MEM supplemented with 10% FBS, and the cells were incubated for an additional hours. Posttransfection, cells were fixed for 10 minutes in cold 4% formaldehyde/ PBS+5 mM MgCl$_2$ and processed to detect β-galactosidase, according to the method of Lim et al. (*Biotechniques* 7:576–579 (1989)). In control experiments, we have shown that the transfection conditions do not appreciably reduce the percent of cells with peripherally localized endogenous β-actin mRNA.

The transfection, staining, and statistical analysis were done as described by Kislauskis et al. (supra). After transfection, cells on coverslips were washed with PBS solution, fixed for 10 min at room temperature in 4% paraformaldehyde in PBS/5 mM MgCl$_2$, rinsed in PBS, and stored in 70% ethanol at 4° C. For methods where enzyme activity and the reporter in RNA were detected simultaneously, nick-translated probes were generated using standard procedures (Lawrence et al. (1989), supra). To detect endogenous actin mRNAs, coverslips were hydrated in PBS/5 mM MgCl$_2$, and then hybridized overnight (~12 h) at 37° C. with 20 ng of nick-translated digoxigenin-labeled β-actin cDNA sequences 95–1477. To detect Lac Z reporter mRNAs, each coverslip was hybridized to 20 ng of digoxigenin-labeled, nick-translated RSVβgal plasmid overnight at 37° C. Anti-digoxigenin conjugated to alkaline phosphatase was diluted 1:250 in PBS containing 2 mg/ml BSA (Boehringer Mannheim, Indianapolis, Ind.). Alternatively, in a double-label in situ hybridization procedure, a primary antibody anti-digoxigenin HRP to detect endogenous actin mRNA (Boehringer Mannheim) at a 1:250 dilution in PBS plus 0.2% BSA was incubated for 30 minutes at 37° C., washed, subsequently stained with diaminobenzidine (DAB), and amplified by silver enhancement using the AMP B Silver Enhancement Kit (DIGENE, Silver Spring, Md.). This was used simultaneously with the β-galactosidase reaction to identify the distribution of fusion transcript. Cellular actin was stained after fixation with FITC-conjugated phalloidin (Molecular Probes, Inc., Eugene, Oreg.).

Probes for In Situ Hybridization

Six oligonucleotide probes (50–55 bases) specific to β-actin mRNA were synthesized on a DNA synthesizer (model 396; Applied Biosystems, Foster City, Calif.). Five amino-modified thymidine residues (Glen Research, Sterling, Va.) were incorporated approximately every 10 bases. Incorporation of fluorochromes less than every 10 bases causes quenching of the fluorescent signal. After deprotection, probes were gel-purified on a 10% polyacrylamide gel, and then labeled with a specific fluorochrome. Oligonucleotides complementary to β-actin mRNA were labeled with Cy-3 (Biological Detection Lab, Pittsburgh, Pa.) in 0.1M NaHCO$_3$/Na$_2$CO$_3$, pH 9.0, overnight, in the dark, at room temperature, and then fractionated on a Sephadex G-50 column. Fractions were combined, lyophilized, and further purified on 10% polyacrylamide native gels. The sequences of the six β-actin oligos, i.e., KLT-4, KLT-15, KLT-18, KLT-19, KLT-20 and KLT-23, have been published by Taneja et al. (supra).

Antisense Oligonucleotides

Antisense treatment was performed on CEFs grown, as described above, to ca. 50% confluence in OPTI-MEM I medium (GIBCO BRL) containing 10% FBS. Phosphorothioate oligonucleotides were synthesized on a DNA synthesizer model 396 (Applied Biosystems, Foster City, Calif.). The oligonucleotides were purified through CEPACK columns (Millipore, Milford, Mass.), lyophilized overnight, and resuspended in DEPC-treated distilled water. Each oligonucleotide was added to the complete medium (OPTI-MEM I supplemented with 10% FBS). Experiments that required 12-hour exposure to these antisense oligonucleotides involved three treatments of 4 hours each, in 1.0 ml complete medium.

The antisense oligonucleotides tested are described below. The letter designations correspond to the designations in FIG. 4. The position numbers refer to the nucleotide positions in the chicken β-actin 3' UTR. Our antisense molecules were as follows:

Oligonucleotide A (positions 1222–1239): 5' TGGTAA-CAGT CCGGTTTA 3' (SEQ ID NO:24);

Oligonucleotide B (positions 1240–1260): 5' TCATCA-CAGG GGTGTGGGTGT 3' (SEQ ID NO:25);

Oligonucleotide C (positions 1261–1278); 5' GCATT-TATGG GTTTTGTT 3' (SEQ ID NO:26);

Oligonucleotide D (positions 1279–1297): 5' ATCCT-GAGTC AAGCGCCA 3' (SEQ ID NO:27);

Oligonucleotide E (positions 1412–1432): 5' CTCA-GATCGC TTGTAGAACTT 3' (SEQ ID NO:28); and Oligonucleotide F (positions 1433–1453): 5' AACAAAT-GTA CAATCAAAGTC 3' (SEQ ID NO:29).

To verify that the observed delocalization activity of the antisense oligonucleotides corresponding to zipcode regions were strand-specific, we synthesized and tested a sense oligonucleotide, Oligonucleotide C+ (SEQ ID NO:30), whose sequence complements antisense Oligonucleotide C and corresponds to the sense (mRNA) sequence (positions 1261–1278) .

FIGS. 5A–5H illustrate the results of the antisense oligonucleotide treatments carried out on CEFs. Control CEFs not treated with any oligonucleotide (FIG. 5G), CEFs treated with antisense oligonucleotide D, which is directed to a non-zipcode sequence in the 3' UTR (FIG. 5E), and CEFs treated with sense oligonucleotide C+ (FIG. 5C), showed localized actin mRNA at the leading lamellae and polarized cell phenotypes, with actin filaments oriented toward the lamellipodia. In contrast, CEFs treated with antisense oligonucleotide C showed nonlocalized actin mRNA, nonpolarized phenotypes, and actin stress fibers oriented in many directions.

RNA (Northern) Analysis Procedure

Total RNA was extracted from CEFs using TRI Reagent (Molecular Research Center, Inc., Cincinnati, Ohio) in accordance with the vendor's recommendations. The total RNA was resolved in a 1% agarose/2.2M formaldehyde gel before blotting onto ZetaProbe (BioRad Labs., Hercules, Calif.). One blot was hybridized overnight to $^{32}$P-labeled antisense riboprobe generated from the human GAPDH cDNA insert (Clonetech, Palo Alto, Calif.) at 37° C., washed, and exposed 30 minutes to film without a screen. Subsequently, chemiluminescence was performed to detect actin mRNA on the same blot. Initially the blot was stripped in 5 mM EDTA for 50 min in boiling water, and then prehybridized at 37° C. in 50% formamide, 5×SSC, 0.5% SDS, 5×Denhardt's, and 50 mM NaPO$_4$ for 2 h. Digoxigenin-labeled actin probes (250 ng) were added and hybridized at 37° C. for 12 h in the prehybridization solution plus 1% dextran sulfate. The filter was washed as described above, and then in 1% Blocking Reagent in 150 mM NaCl/50 mM Tris pH 7.5 (buffer 1, Boehringer Mannheim) for 30 min at room temperature (RT). Antidigoxigenin conjugated to alkaline phosphatase (Boehringer Mannheim) was diluted (1:2,500) in 20 ml of blocking buffer and incubated for 30 min at RT. The unbound antibody was washed from the filter, and the filter was rinsed in buffer 3 without MgCl$_2$, and chemiluminescent substrate was diluted (Immunolite Assay Kit, Biorad Labs.), and the blot was incubated in the presence of the substrate for 5 minutes at room temperature before exposing it to film at room temperature. A separate preparation of total RNA from similarly treated CEFs was blotted as above and probed with a gel-isolated, random-primed, β-actin 3' UTR sequences (positions 1193–1814) with specific activity of 5×10$^6$ cpm/ml (Boehringer Mannheim), washed as described above, and exposed to film for 1 hour at −80° C.

Protein Analysis Procedures

CEFs were labeled after a 12-h treatment with the various oligonucleotides for 30 minutes with 150 µCi/ml L-[$^{35}$S] methionine (Amersham Corp., Arlington Heights, Ill.) in MEM supplemented with L-leucine and L-lysine (GIBCO BRL). Equal TCA-precipitable counts were electrophoresed through 10% SDS-polyacrylamide gel using standard procedures (SEQUAGEL, National Diagnostics, Atlanta, Ga.). The gel was fixed and silver stained using Silver Stain plus Kit (BioRad Labs.), and then dried, treated with Amplify (Amersham Corp.) for 30 minutes, and exposed to film at −70° C. with enhancing screens. Immunoprecipitation of β-actin from the same extract involved incubation of equal TCA-precipitable counts with saturating concentration of H2 anti-β-actin antisera (10 µl) (Otey et al., *J. Cell Biol.* 34:113–124 (1987)) at 4° C. overnight on an orbital rocker before the addition of 75 µl of precleared protein G-Sepharose (Sigma Chem. Co., St. Louis, Mo.) and an additional 2-hour incubation at 4° C. After a brief centrifugation at 14,000 rpm, the pellet was resuspended in 2×sample buffer, boiled for 2 minutes and loaded as above.

Structural Properties of the β-Actin RNA Zipcode

Figure 1A:
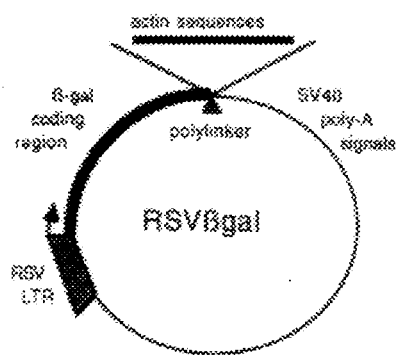
FIG. 1B is a photograph showing endogenous actin mRNA distribution in a CEF exposed to transfection conditions. Detection was by a digoxigenin-labeled cDNA probe for β-actin mRNA sequences.
FIG. 1C is a photograph showing the non-localized distribution of β-galactosidase activity in a cell transfected with the RSVβgal plasmid containing no β-actin insert.
FIG. 1D is a photograph showing the localization of β-galactosidase activity in a cell transfected with the RSVβgal plasmid containing a full-length β-actin mRNA fused to the reporter gene.
Figure 1B:
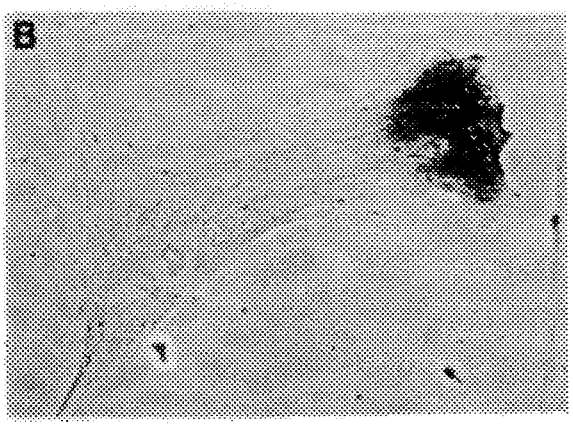
Figure 1C:
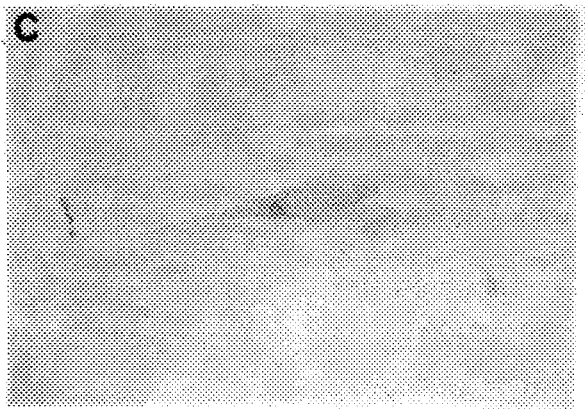
Figure 1D:
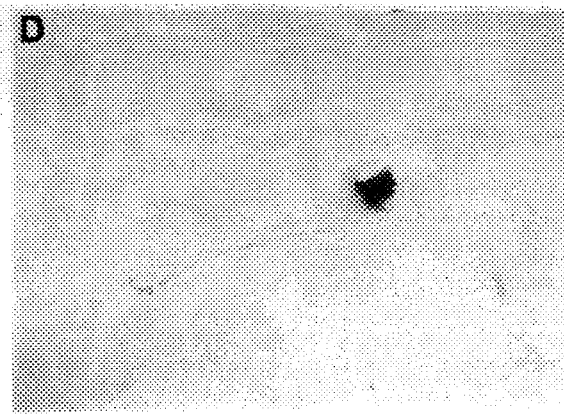

In nearly all cells (94%) transfected with the vector alone (FIG. 1C), β-galactosidase activity (blue staining) was found to be nonlocalized, throughout the cytoplasm. In marked contrast, a significant number of transfectants (33%), expressing reporter transcripts fused to the entire chicken actin cDNA (~1.8 kb), showed blue staining prominently in the peripheral cytoplasm (FIG. 1D). This magnitude was similar to the endogenous level of actin mRNA localization (Kislauskis et al., 1993; Latham et al., 1994). In situ hybridization was performed using probes specific for β-galactosidase coding sequences after staining with X-gal to reveal that the distribution of reporter RNA correlated with the distribution of β-galactosidase activity in the same transfectant. Thus, intracellular β-galactosidase activity was an accurate indicator of the LacZ mRNA distribution in our transient assay. These data provided a statistically significant basis for assessing RNA localization sequences. In addition, the enzymatic assay was more rapid and convenient than in situ hybridization.

Using the spatial expression characteristics of these chimeric gene products, a 54-nucleotide zipcode was mapped to the 3'UTR of β-actin, proximal to the coding region. A series of 3'-deletions and subcloned fragments of the β-actin cDNA were evaluated for their ability to target β-galactosidase activity to the leading edge of transfected CEFs (FIG. 2). A significant 5.8-fold (32.6%/5.6%) increase in localization over the vector was found using the full-length β-actin insert fused to β-galactosidase (p<0.0002). Equally significant increases in localization were found with two 3'-exonuclease deletion constructions, construct B with 458 of 591 nucleotides of 3'UTR deleted, and construct C with 536 nucleotides deleted. A 483-bp fragment containing 43 nucleotides of coding sequence through 440 nucleotides of the 3'UTR (construct D) also localized as well (6.9-fold). In construct C, all but the first 54 nucleotides of the 591 nucleotide 3'UTR were removed from the full-length β-actin cDNA. Further deletion of the entire 3'UTR plus 20 nucleotides of coding region (construct E) resulted in a level of activity indistinguishable from the vector control (p=1.0). When evaluated separately, the last 20 nucleotides of β-actin coding region and its entire 3'UTR (construct F) was sufficient to target β-galactosidase activity to the peripheral cytoplasm as well as the full-length actin cDNA and highly significant relative to the vector control (p<0.0002). Overall, these results indicated that the zipcode existed proximal to the stop codon.

Three synthetic oligonucleotides were evaluated: the zipcode within the first 54 nucleotides of the 3'UTR, including the stop codon (construct G), and sequences flanking this zipcode in the coding region (construct H) and in the 3'UTR (construct I). Peripheral localization activity directed by construct G was comparable to the full-length cDNA (p<0.0002). The activities of the flanking regions (constructs H and I) were not significantly different from either the vector alone or the 5'UTR plus coding region (p>0.99 in all cases). Therefore, the first 54 nucleotides of the β-actin 3'UTR was sufficient to target a heterologous mRNA to the peripheral cytoplasm.

To determine if the zipcode was the sole element necessary for localization, it was deleted from full-length β-actin cDNA (construct J). Its removal significantly reduced, but did not eliminate, localization activity relative to the full-length insert. Activity was contained within the remaining 3'UTR fragment (construct K) and was significant relative to the vector (p<0.24). Within that segment, homologies with the 54-nucleotide zipcode were evident in a 43-nucleotide sequence (construct L) which contained half the localization activity of the 54-nucleotide zipcode (17 vs 33%) and was significant relative to the vector (p<0.79).

To ascertain whether the 54- and 43-nucleotide segments were the sole localization determinants, both were deleted from the full-length insert (construct M). This double mutant (construct M) was incapable of localizing β-galactosidase; its activity was indistinguishable from the vector alone. Therefore, only these two segments function to target β-acin mRNA to the peripheral cytoplasm. Because the first 54 nucleotides of the 3'UTR contained activity comparable to the entire β-actin cDNA, we refer to it as the "peripheral RNA zipcode". The 43-nucleotide segment with submaximal activity and homology to the peripheral RNA zipcode is composed of "zipcode elements".

To test orientation dependence, the 54-nucleotide zipcode was inverted (construct N). Inversion of the zipcode reduced localization activity from 33% to 11% of the transfectants, a level which was not significantly different from the vector (p>0.81).

To address the question of position dependence, the zipcode was inserted into the 5'UTR of the LacZ reporter gene. Because of a shift in the reading frame, β-galactosidase was not translated when the zipcode was inserted into the LacZ 5'UTR in the normal orientation. Localization activity in this case was evaluated by in situ hybridization. Quantitation of transfectants showed weak but significant localization activity (15%), relative to the vector alone, when inserted into the 5'UTR. Possibly, insertion of the zipcode sequences upstream of the LacZ coding region may inhibit ribosome-scanning or zipcode-binding protein function, or both. In either case, it appears from these results that zipcode function is orientation-dependent and position-dependent, within the mRNA.

Fine Structure of the Zipcode

Sequence homology between the 54- and 43-nucleotide segments might be expected to identify the minimal zipcode sequence. Two motifs, GGACT and AATGC, are present in both segments (FIG. 3). The GGACT motif occurs at the 5'-end and the AATGC motif occurs at the 3'-end of the 54-nucleotide zipcode.

To determine whether the sequences between these motifs function in localization, positions 10 through 40 in the 54-nucleotide zipcode were deleted (construct O). Deletion of those sequences reduced localization activity (20.9%), comparable to the 43-nucleotide segment (p=1.0), but significantly different from the vector alone (p<0.085). This suggested that the sequences between position 10 and 40 are important for enhancing localization. The two ACACCC motifs removed from the 54-nucleotide segment (construct O) contribute to its activity. A two base deletion of the 54-nucleotide zipcode (construct P) which removed the A and T residues adjacent the AATGC motif was tested. This resulted in reduced localization activity (16%), significantly different from the 54-nucleotide zipcode (p<0.002), indicating the importance of the 3'-motif sequence for localization.

To test the contribution of the two motifs, independently, each was synthesized as a cassette and evaluated. Both the GGACT motif (inserted as TAAACCGGACTGT) and the AATGC motif (inserted as AACCCATAAATGC) (SEQ ID NO:33) were each found to contain weak localization activity (15.2±2.3% and 19.3±7.2%, respectively). Their activities were not significantly different from each other or the combination of the two together in construct O (p=1.0 in all cases). However, localization activity of the 5' motif GGACT was slightly less significant than the 3' motif relative to the vector alone (p<0.129 and p<0.002, respectively). The size or number of zipcode motifs may also be important for maximal localization.

To determine whether these motifs inserted as tandem repeats would function more efficiently, the vector containing three copies of the GGACT motif, in the context of the first 10 nucleotides of the 3'UTR and stop codon, and the vector containing four copies of the AATGC motif, in the context of the last 13 nucleotides of the zipcode, were evaluated separately. Both constructs bearing tandem copies of each motif showed enhanced localization activity. Four copies of the 3' motif (AATGC) localized almost as effectively as the entire intact zipcode (27.5±16.%), while three copies of the 5' motif (GGACT) had somewhat less activity (20.7±8.9%). These data indicated that the elements which comprise the entire 54-nucleotide zipcode each contain submaximal localization activity. The weak localization activity of at least one motif in the zipcode can substitute for the activity of the entire zipcode when multimerized. The high A/C content in the 54-nucleotide zipcode, contained within both 5' and 3' motifs, appearing as AAACC, ACACCC, or AACAAA, may play a part in the mechanism of β-actin mRNA localization. The zipcode, therefore, appears to be composed of several minimal motifs, each of which adds proportionately to the localization.

Conservation of Zipcodes

Further insight into essential sequences required for zipcode function was revealed by comparing the chicken zipcode with the homologous region of the human β-actin cDNA. The mechanisms of RNA localization, and, hence the zipcode sequences, would be expected to be conserved between chicken and human β-actin, since primary cultures of human fibroblasts also localize β-actin mRNA to the leading lamellae (Kislauskis, E. H., unpublished data). A strong selective pressure to retain these functional elements would explain regions of high conservation among the 3'UTRs of vertebrate β-actin genes (Ponte et al., *Mol. Cell Biol.* 3:1783–1791 (1983); Yaffie et al., *Nucleic Acids Res.*, 13:3723–3737 (1985)). More conservation occurs in the 5' region of the 3'UTR, where the zipcodes reside. For example, the first 54 nucleotides of the 3'UTRs of the chicken and human β-actin genes display 65% identity. The first 54 nucleotides of the 3'UTRs of the chicken and human β-actin genes are compared in FIG. 8.

Consistent with a conservation of nucleotide sequence between β-actin 3'UTR regions, we found that zipcode function was similarly conserved. The first 54 nt of the human β-actin 3'UTR (construct Q) localized β-galactosidase in chicken cells quantitatively indistinguishable from the homologous segment of the chicken 3'UTR (28%). This suggests that the cellular mechanism of zipcode function and specificity has been conserved evolutionarily. As illustrated in FIG. 8, an alignment of the chicken and human zipcode sequences reveals considerable homology particularly at the 3' end of the 54-nucleotide segment, where eight consecutive nucleotides occur in a conserved region of 13/16 (81% identity). This supports and confirms the importance of this element in localizing the mRNA, as was shown with the genetic chimeras. In particular, the AATGC motif, described above is represented in the human sequence as AACTTGC. It is possible that these conserved sequences represent elements of the zipcode which are essential for maximal localization activity. Complementary pair of oligonucleotides were synthesized, fused to LacZ, and tested in CEFs (construct Q). Because this construct functioned as well in chicken cells as the chicken zipcode (28%), it confirmed the conservation of the RNA zipcode mechanism. Furthermore, conserved sequences between these diverse species are likely to be required for the mechanism. Alignment of these sequences showed short stretches throughout the zipcode, some as long as 8 nucleotides. Therefore, this confirms that the zipcode is composed of multiple dispersed elements which act in concert to provide maximal activity.

Functional Properties of the β-Actin RNA Zipcode

To confirm the role of the zipcode in localizing endogenous actin mRNA, phosphorothioate-modified oligonucleotides were used as antisense to inhibit zipcode function. The effects of these modified oligonucleotides (18-mers) on actin mRNA localization and cell phenotype was assessed after a 12-hour treatment. The positions and orientations relative to the β-actin RNA zipcode are diagrammed schematically (FIG. 4). Treatment with antisense oligonucleotides corresponding to zipcode sequences resulted in a suppression of β-actin mRNA localization relative to untreated CEFs, while a sequence flanking the zipcode and a sense sequence had no effect. In particular, oligo C (the 3' end of the zipcode) reduced the percent of CEFs with a peripheral distribution of actin mRNA to 21% of control. Antisense oligonucleotides A and B (the 5' two-thirds) were less effective (33 and 37% of control, respectively). Similarly, oligonucleotides complementary to the 5' half (oligo E) and 3' half (oligo F) of the 43-nucleotide RNA zipcode element reduced localized actin mRNA, to 51 and 29%, respectively. In striking contrast, neither the 3'UTR sequences flanking the 54-nucleotide segment (oligo D) nor the sense strand of the most effective inhibitory probe (oligo C+) reduced actin mRNA localization relative to control, (91 and 98%, respectively). These data add strong support to the role of the RNA zipcode in endogenous β-actin mRNA localization to the cell periphery.

The effects of antisense treatment on actin mRNA distribution are illustrated in FIG. 5 (A, C, E and G). A normal peripheral distribution of actin mRNA and characteristic polarized phenotype were maintained in untreated CEFs (control) and CEFs treated with oligo C+ (zipcode sense) and oligo D (flanking the zipcode). In contrast, CEFs treated with oligo C (the 3' end of the zipcode) showed a nonlocalized, homogenous distribution of actin mRNA and a change to a nonpolarized morphology. In addition, cells treated with oligo C became stellate in shape with collapsed lamellae and were less well spread, suggesting a reduced adhesion to the substrate. These data imply that the asymmetric distribution of actin mRNA localization may be reflected in a concomitant structural asymmetry, most likely of the actin cytoskeleton.

To assess the distribution of actin filaments after incubation with the antisense oligonucleotides, CEFs were stained with phalloidin. This is shown in FIG. 5 (B, D, F and H). Unlike control cells and cells treated with oligo D, where actin staining is concentrated within the leading edge, and stress fibers are polarized toward the leading lamellae, CEFs treated with oligo C showed no leading edge and little actin staining at the periphery; the actin filament system was organized perinuclearly. Thus, the actin cytoskeleton reorganized after treatment with antizipcode oligo C, but not with the sense strand (oligo C+), or a flanking sequence (oligo D).

To determine whether the steady state level or integrity of actin mRNA was affected by the antisense oligonucleotide treatment, Northern blot analysis was performed on total RNA extract from CEFs after each antisense oligonucleotide treatment (FIG. 6A). Actin mRNA levels were compared directly to an internal standard, GAPDH mRNA. No substantial change in steady state levels of actin mRNA was observed (±15%) relative to the GAPDH. Moreover, the Northern analysis revealed no change in the size distribution of action mRNA after incubation with the antisense oligonucleotides which indicate that RNAse H-mediated degradation did not occur. Therefore, the inhibition of action mRNA localization is not due to an effect on mRNA stability or integrity. This was confirmed with a separate Northern blot of RNA from similarly treated CEFs probed with β-actin 3'UTR sequences, showing no change in β-actin mRNA quantity or quality.

There are at least two mechanisms by which antizipcode oligonucleotides could affect actin expression, and, thereby, cell phenotype. First, inappropriately localized actin mRNA may suppress actin protein synthesis. Over the 12-hour treatment, this could deplete the cellular pool of G-actin. Alternatively, nonlocalized actin mRNA could affect the site of actin protein synthesis, and consequently influence sites of actin polymerization.

To distinguish between these possibilities, CEFs were treated with each oligonucleotide for 12 h, pulse-labeled with [$^{35}$S]methionine, and extracted. No change in total cellular actin synthesis (<14%) relative to a 29-kD band on the autoradiogram was observed among the various antisense probes (FIG. 6B).

To address the question of whether expression of the β-actin isoform was specifically effected by this treatment, equal counts of the same extracts were immunoprecipitated using a β-actin specific antibody. Quantitation of the 43-kD β-actin band in each case relative to the untreated control extract indicated no significant effect in β-actin synthesis. Therefore, the striking change in cell phenotype that resulted from exposure to an antisense oligonucleotide (oligonucleotide C, FIGS. 5A and 5B) could not be due to its effect on actin synthesis per se. Rather, we conclude that the consequence of treatment with antizipcode oligonucleotides on cell phenotype resulted from a change in the site of β-actin synthesis, and hence, the site of actin concentration within the cell. These data indicate that the RNA zipcode directs β-actin mRNA to the cell periphery, where the protein synthetic apparatus can provide a compartmentalized source of G-actin to facilitate the assembly of actin filaments involved in the maintenance of cell structure, polarity, and motility.

While we have described a number of embodiments of this invention, it is apparent that our basic constructions can be modified to provide other embodiments that utilize the processes and products of this invention. Therefore, it must be appreciated that the scope of this invention is defined by the appended claims rather than by the specific embodiments that have been presented by way of example.

---

We claim:

1. A method for inhibiting the intracellular localization of a target mRNA molecule to the periphery of a target cell in vitro, comprising introducing into the target cell an antisense oligonucleotide that is from 10 to 50 nucleotides long and is complementary to a region of a zipcode located in the 3' untranslated region of the target mRNA molecule, wherein the complementarity involves base pair mismatches constituting not more than 10% of the total number of nucleotides in the antisense oligonucleotide molecule.

2. The method according to claim 1, wherein the antisense oligonucleotide is complementary to a region of a zipcode selected from the group consisting of: (SEQ ID NO:1) and (SEQ ID NO:2).

3. The method according to claim 2, wherein the antisense oligonucleotide has a nucleotide sequence selected from the group consisting of (SEQ ID NO:24), (SEQ ID NO:25), (SEQ ID NO:26), (SEQ ID NO:28) and (SEQ ID NO:29).

4. The method according to claim 1, wherein the antisense oligonucleotide comprises one or more phosphorothioate deoxynucleotides.

5. An antisense oligonucleotide molecule having a length between 10 and 50 nucleotides, said antisense oligonucleotide having a nucleotide sequence complementary to a portion of the sequence (SEQ ID NO:1), wherein said portion is between about 5 and 50 nucleotides in length, and wherein the complementarity involves base pair mismatches constituting not more than 10% of the total number of nucleotides in the antisense oligonucleotide molecule.

6. An antisense oligonucleotide molecule having a length between 10 and 50 nucleotides, said antisense oligonucleotide having a nucleotide sequence complementary to a portion of the sequence (SEQ ID NO:2), wherein said portion is between about 5 and 43 nucleotides in length, and wherein the complementarity involves base pair mismatches constituting not more than 10% of the total number of nucleotides in the antisense oligonucleotide molecule.

\* \* \* \* \*

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:

( A ) LENGTH: 54 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

ACCGGACTGT TACCAACACC CACACCCCTG TGATGAAACA AAACCCATAA ATGC    54

( 2 ) INFORMATION FOR SEQ ID NO:2:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

AAGTTCTACA ATGCATCTGA GGACTTTGAT TGTACATTTG TTT    43

( 2 ) INFORMATION FOR SEQ ID NO:3:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "PCR PRIMER"

( x i ) SEQUENCE DESCRIPTION: SEQ ID NO:3:

GGACTAGATG CGCATAAAAC AAGACG    26

( 2 ) INFORMATION FOR SEQ ID NO:4:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "PCR PRIMER"

( x i ) SEQUENCE DESCRIPTION: SEQ ID NO:4:

TTGCGGCCGC TCAGTGTACA GGTAGCCCCT    30

( 2 ) INFORMATION FOR SEQ ID NO:5:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "PCR PRIMER"

( x i ) SEQUENCE DESCRIPTION: SEQ ID NO:5:

GGACTAGATG CGCATAAAAC AAGACG    26

( 2 ) INFORMATION FOR SEQ ID NO:6:

( i ) SEQUENCE CHARACTERISTICS:
( A ) LENGTH: 30 base pairs
( B ) TYPE: nucleic acid

```
        ( C ) STRANDEDNESS: single
        ( D ) TOPOLOGY: linear ( i i ) MOLECULE TYPE: other nucleic acid
            ( A ) DESCRIPTION: /desc = "PCR PRIMER"

( x i ) SEQUENCE DESCRIPTION: SEQ ID NO:6:
```

TTGCGGCCGC TCAGTGTACA GGTAGCCCCT          30

( 2 ) INFORMATION FOR SEQ ID NO:7:

```
    ( i ) SEQUENCE CHARACTERISTICS:
            ( A ) LENGTH: 29 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "PCR PRIMER"

( x i ) SEQUENCE DESCRIPTION: SEQ ID NO:7:
```

GGTCTAGAGC ATAAAACAAG ACGAGATTG           29

( 2 ) INFORMATION FOR SEQ ID NO:8:

```
    ( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "PCR PRIMER"

( x i ) SEQUENCE DESCRIPTION: SEQ ID NO:8:
```

GGAAGCTTAG AACTTTGGGG GCGT                24

( 2 ) INFORMATION FOR SEQ ID NO:9:

```
    ( i ) SEQUENCE CHARACTERISTICS:
            ( A ) LENGTH: 28 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "PCR PRIMER"

( x i ) SEQUENCE DESCRIPTION: SEQ ID NO:9:
```

TTGGGCGCTA TTGTGTGCAC TTTTATTT            28

( 2 ) INFORMATION FOR SEQ ID NO:10:

```
    ( i ) SEQUENCE CHARACTERISTICS:
            ( A ) LENGTH: 62 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "SYNTHETIC OLIGONUCLEOTIDE"

( x i ) SEQUENCE DESCRIPTION: SEQ ID NO:10:
```

GATCCTAAAC CGGACTGTTA CCAACACCCA CACCCTGTGA TGAAACACCC CCCATAAATG          60

CT                                                                        62

( 2 ) INFORMATION FOR SEQ ID NO:11:

```
    ( i ) SEQUENCE CHARACTERISTICS:
```

( A ) LENGTH: 63 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC OLIGONUCLEOTIDE"

( x i ) SEQUENCE DESCRIPTION: SEQ ID NO:11:

CTAGAGCATT TATGGGTTTT GTTTCATCAC AGGGGTGTGG GTGTTGGTAA CAGTCCGGTT    60

TAG    63

( 2 ) INFORMATION FOR SEQ ID NO:12:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC OLIGONUCLEOTIDE"

( x i ) SEQUENCE DESCRIPTION: SEQ ID NO:12:

CATCCGCAAG CAGGAGTACG ATGAATCCGG ACCCTCCATT GTCCACCGCA AA    52

( 2 ) INFORMATION FOR SEQ ID NO:13:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC OLIGONUCLEOTIDE"

( x i ) SEQUENCE DESCRIPTION: SEQ ID NO:13:

GATCTTTGCG GTGGACAATG GAGGGTCCGG ATTCATCGTA CTCCTGCTTG CG    52

( 2 ) INFORMATION FOR SEQ ID NO:14:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC OLIGONUCLEOTIDE"

( x i ) SEQUENCE DESCRIPTION: SEQ ID NO:14:

CTAGAAACAA GACGAGATTG GCATGGCTTT ATTTGTTTTT TCTTTTGC    48

( 2 ) INFORMATION FOR SEQ ID NO:15:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC OLIGONUCLEOTIDE"

( x i ) SEQUENCE DESCRIPTION: SEQ ID NO:15:

GGCCGCAAAA GAAAAAACAA ATAAAGCCAT GCCAATCTGG TCTTGTTT    48

( 2 ) INFORMATION FOR SEQ ID NO:16:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC OLIGONUCLEOTIDE"

( x i ) SEQUENCE DESCRIPTION: SEQ ID NO:16:

```
GATCCCAAGT TCTACAATGC ATCTGAGGAC TTTGATTGTA CATTTGTT                48
```

( 2 ) INFORMATION FOR SEQ ID NO:17:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:17:

```
CTAGAACAAA TGTACAATCA AAGTCCTCAG ATGCATTGTA GAACTTGG                48
```

( 2 ) INFORMATION FOR SEQ ID NO:18:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:18:

```
GATCCTAGGC GGACTATGAC TTAGTTGCGT TACACCCTTT CTTGACAAAA CCTAACTTGC   60
GCT                                                                63
```

( 2 ) INFORMATION FOR SEQ ID NO:19:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:19:

```
CTAGAGCGCA AGTTAGGTTT TGTCAAGAAA GGGTGTAACG CAACTAAGTC ATAGTCCGCC   60
TAG                                                                63
```

( 2 ) INFORMATION FOR SEQ ID NO:20:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "ZIPCODE ELEMENT"

( x i ) SEQUENCE DESCRIPTION: SEQ ID NO:20:

AGTCTACAGT CCGGTTTAG                                                          19

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "ZIPCODE ELEMENT"

(xi) SEQUENCE DESCRIPTION: SEQ ID NO:21:

AGTCTACAGT CCGGTTTAG                                                          19

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "ZIPCODE ELEMENT"

(xi) SEQUENCE DESCRIPTION: SEQ ID NO:22:

GATCCAACCC ATAAATGCA                                                          19

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "ZIPCODE ELEMENT"

(xi) SEQUENCE DESCRIPTION: SEQ ID NO:23:

GATCTGCATT TATGGGTTG                                                          19

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "ANTISENSE OLIGONUCLEOTIDE"

(xi) SEQUENCE DESCRIPTION: SEQ ID NO:24:

TGGTAACAGT CCGGTTTA                                                           18

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "ANTISENSE OLIGONUCLEOTIDE"

(xi) SEQUENCE DESCRIPTION: SEQ ID NO:25:

TCATCACAGG GGTGTGGGTG T                                                        21

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "ANTISENSE OLIGONUCLEOTIDE"

(xi) SEQUENCE DESCRIPTION: SEQ ID NO:26:

GCATTTATGG GTTTTGTT                                                            18

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "ANTISENSE OLIGONUCLEOTIDE"

(xi) SEQUENCE DESCRIPTION: SEQ ID NO:27:

ATCCTGAGTC AAGCGCCA                                                            18

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "ANTISENSE OLIGONUCLEOTIDE
           (HUMAN SEQUENCE)"

(xi) SEQUENCE DESCRIPTION: SEQ ID NO:28:

CTCAGATCGC TTGTAGAACT T                                                        21

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "ANTISENSE OLIGONUCLEOTIDE
           (HUMAN SEQUENCE)"

(xi) SEQUENCE DESCRIPTION: SEQ ID NO:29:

AACAAATGTA CAATCAAAGT C                                                        21

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SENSE OLIGONUCLEOTIDE"

( x i ) SEQUENCE DESCRIPTION: SEQ ID NO:30:

CGTAAATACC CAAAACAA  18

( 2 ) INFORMATION FOR SEQ ID NO:31:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

GCGGACTATG ACTTAGTTGC GTTACACCCT TTCTTGACAA AACCTAACTT GC  52

( 2 ) INFORMATION FOR SEQ ID NO:32:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

TAAACCGGAC TGT  13

( 2 ) INFORMATION FOR SEQ ID NO:33:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

AACCCATAAA TGC  13